United States Patent [19]

Shai et al.

[11] Patent Number: 5,718,701
[45] Date of Patent: Feb. 17, 1998

[54] ABLATION ELECTRODE

[75] Inventors: Isaac Shai, Springfield, N.J.; Frank E. Marchlinski, Bala Cynwyd; David S. Schwartzman, Fort Washington, both of Pa.

[73] Assignee: Electro-Catheter Corporation, Rahway, N.J.

[21] Appl. No.: 616,969

[22] Filed: Mar. 18, 1996

Related U.S. Application Data

[63] Continuation of Ser. No. 105,497, Aug. 11, 1993, abandoned.

[51] Int. Cl.$^6$ .......................... A61B 17/39; A61B 5/0402
[52] U.S. Cl. .......................... 606/41; 606/49; 607/99; 607/101; 607/102; 607/122; 128/642; 128/734
[58] Field of Search .......................... 607/99, 101, 102, 607/119, 122; 606/41, 45, 49; 128/642, 734, 736

[56] References Cited

U.S. PATENT DOCUMENTS

| | | | |
|---|---|---|---|
| 4,682,596 | 7/1987 | Bales et al. | 606/39 |
| 4,784,596 | 11/1988 | Skalsky et al. | 607/122 |
| 4,848,352 | 7/1989 | Pohndorf et al. | 607/122 |
| 4,955,382 | 9/1990 | Franz et al. | 607/122 |
| 5,080,660 | 1/1992 | Buelna | 606/45 |
| 5,179,946 | 1/1993 | Weiss | 128/734 |
| 5,277,201 | 1/1994 | Stern | 606/41 |
| 5,281,213 | 1/1994 | Milder et al. | 607/122 |
| 5,314,466 | 5/1994 | Stern et al. | 606/41 |
| 5,320,101 | 6/1994 | Faupel et al. | 128/642 |
| 5,454,809 | 10/1995 | Janssen | 606/41 |

FOREIGN PATENT DOCUMENTS

| | | | |
|---|---|---|---|
| 1544396 | 2/1990 | U.S.S.R. | 606/41 |

*Primary Examiner*—Lee S. Cohen
*Attorney, Agent, or Firm*—Cohen, Pontani, Lieberman & Pavane

[57] ABSTRACT

An electrode catheter is provided for ablation of arrhythmogenic tissue in a malperforming heart and includes an elongated catheter tube having longitudinally spaced apart proximal and distal ends. At least one electrode for ablation of the arrhythmogenic tissue in a targeted region of the patient is carried on the catheter tube, preferable at or proximate the distal end of the catheter tube. One such electrode may be located at the distal tip of the catheter and configured in the shape of a generally flat disk that substantially conforms to the contour of the targeted region and such that the ratio of the surface area of the tissue-contacting end face to that of a side wall portion of the electrode is greater than 1.0. A conductor is arranged through the elongated catheter tribe and is coupled with the electrode at the distal end, while an energy source is electrically coupled to the conductor at the proximal end of the catheter tube for supplying energy to the electrode for ablation of the arrhythmogenic tissue. A temperature sensor is disposed in the electrode for dynamically sensing the temperature of the targeted region and for use in controlling the amount Of energy supplied to the electrode tip to maintain a predetermined temperature at the targeted region.

32 Claims, 13 Drawing Sheets

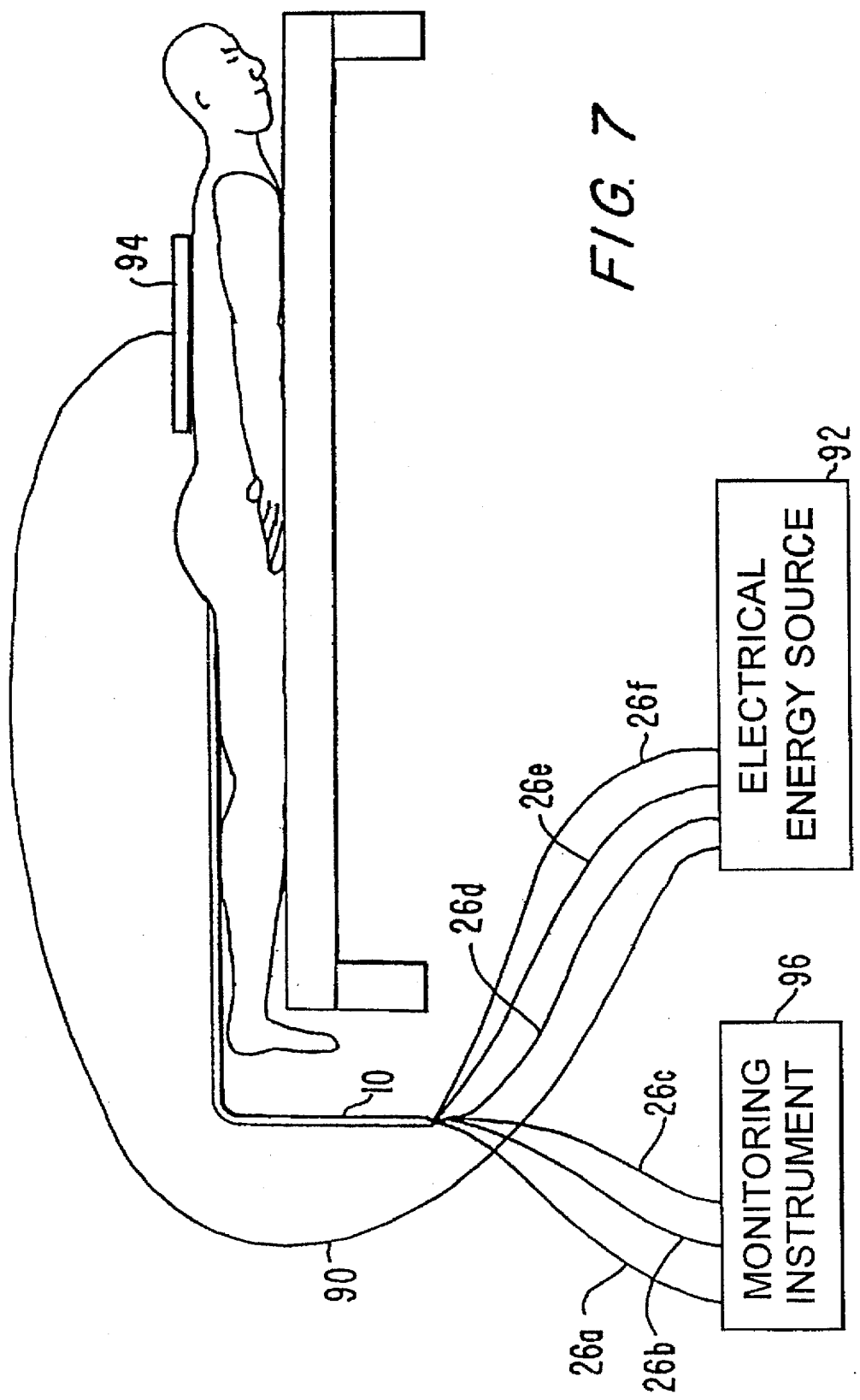

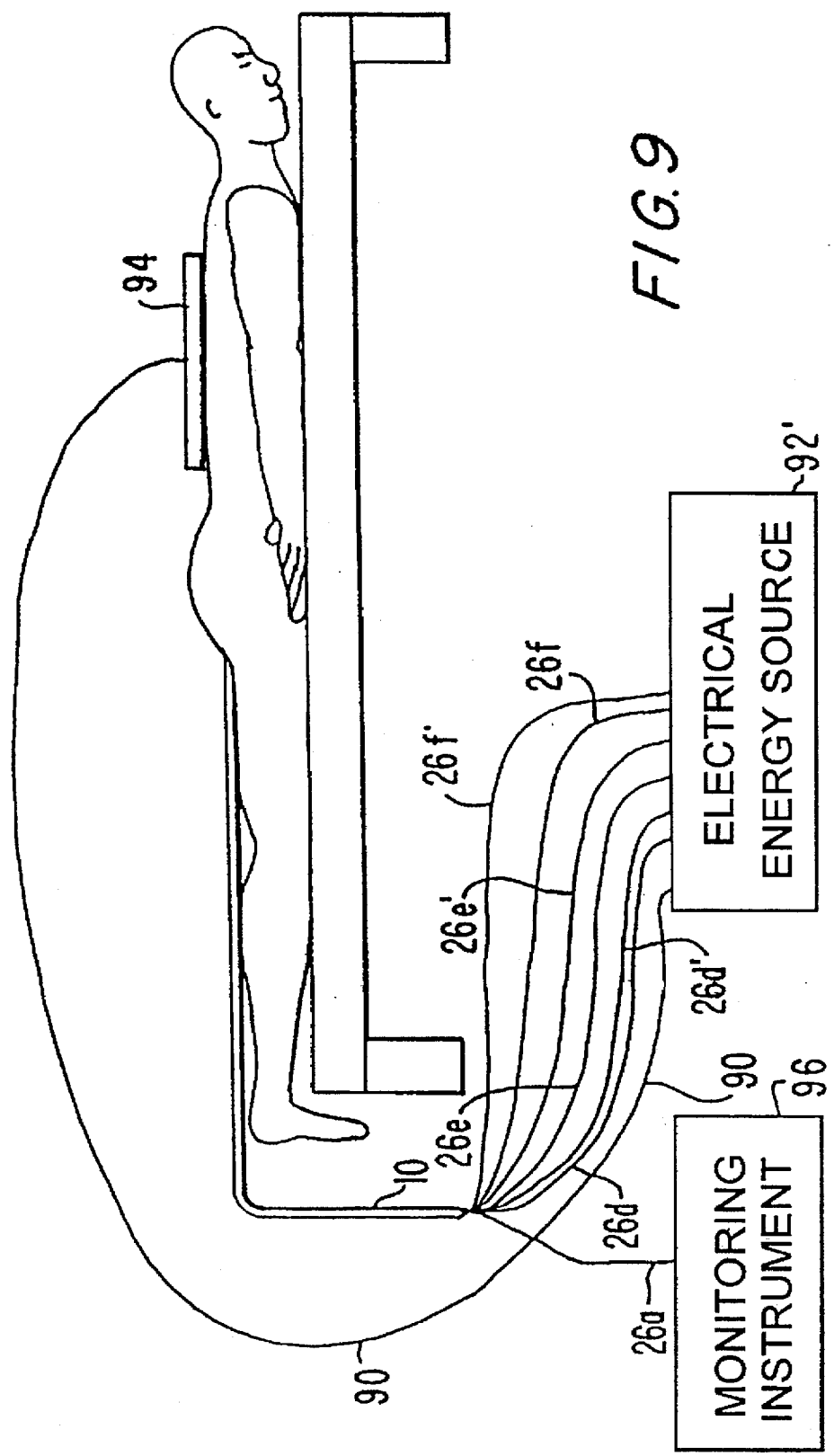

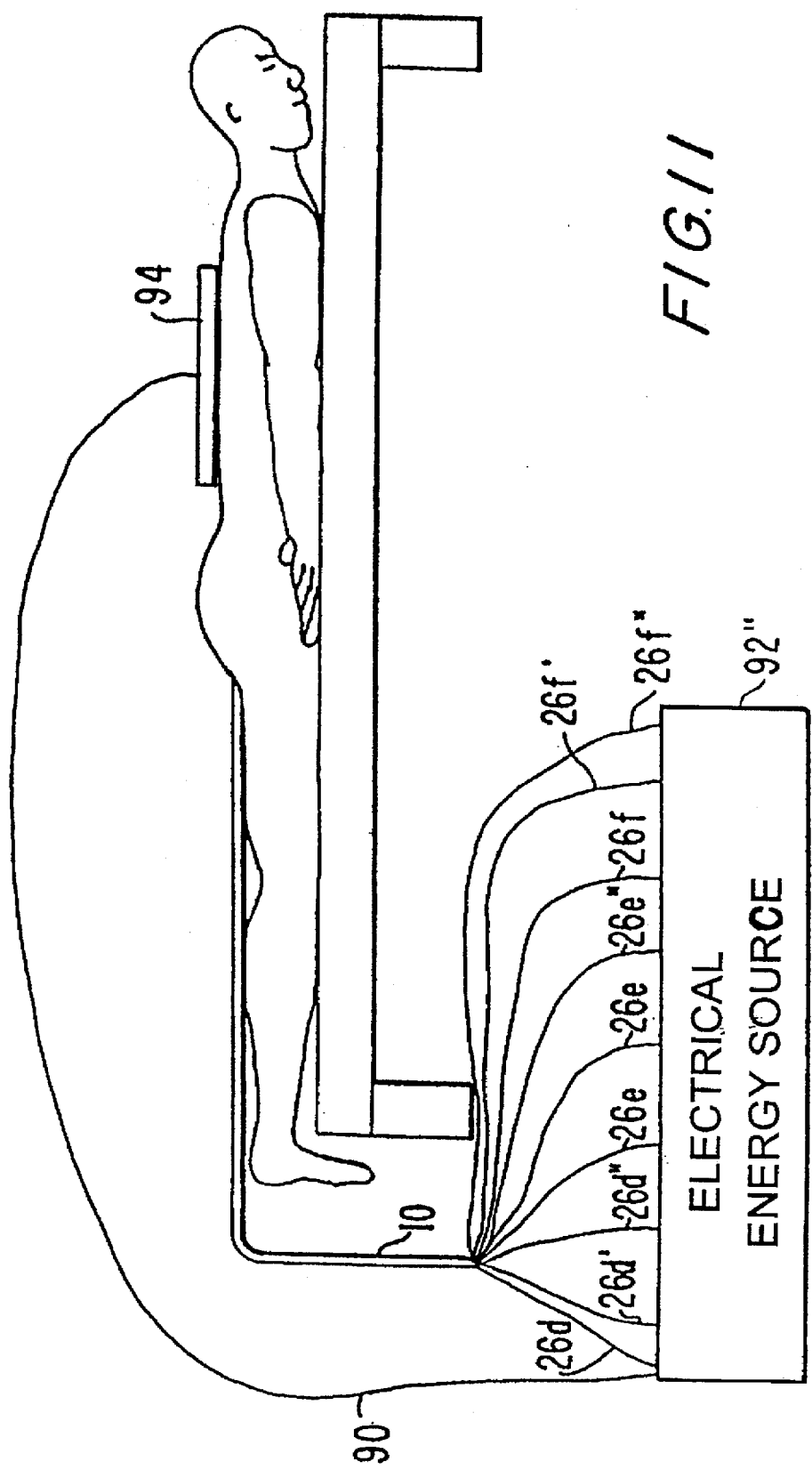

ABLATION ELECTRODE

CROSS-REFERENCE TO RELATED APPLICATION

This application is a continuation of application Ser. No. 08/105,497, filed Aug. 11, 1993, now abandoned.

FIELD OF THE INVENTION

The present invention is directed to an ablation electrode used for ablation of arrhythmogenic tissue generally found in the endocardium and/or myocardium tissue of a malperforming heart. More particularly, the present invention relates to an electrode on a cardio-vascular catheter, most preferably at or proximate the distal end of the catheter, and configured to substantially conform to the endocardial contour of the arrhythmogenic tissue to be treated.

BACKGROUND OF THE INVENTION

The heart contains a system for generating rhythmical impulses-to cause rhythmical contractions of the heart muscle. These impulses are generated in the sino-atrial node of the heart. The heart also contains a means, known as pathways, for conducting these impulses throughout the heart to cause the other portions of the heart to contract. These pathways are generally disposed at or near the surface of the endocardium and are analogous to conductors in an electrical circuit.

Cardiac arrhythmias can occur when arrhythmogenic tissue such as aberrant pathways or ectopic pacing foci develops in the heart. Aberrant pathways provide additional, unintended paths for the rhythmical impulses to pass from one portion of the heart to another and are analogous to detrimental shunt conductors unintendedly connecting or short-circuiting electrical circuit elements. A circuit having unintended shunt conductors does not function properly and does not have the same electrical characteristics as intended or designed. Ectopic foci generate spurious impulses outside the sino-atrial node, which may cause uncoordinated contractions of portions of the myocardium which may interfere with effective pumping of the heart.

Heretofore, patients with arrhythmias have most commonly been treated with medications to control the generation and/or conduction of the abnormal impulses. However, such treatment has been only moderately successful and the medications are relatively expensive and may cause undesirable side effects.

Another type of treatment includes the ablation or cauterization of the arrhythmogenic tissue. The arrhythmogenic tissue is ablated or cauterized to form a lesion, or nonfunctioning tissue volume, and thereby "open circuit" the aberrant pathway or disable the ectopic focus. The ablated pathway does not thereafter transmit or conduct any impulses and the ablated ectopic focus no longer generates spurious impulses. As a result of this treatment, the heart does not exhibit cardiac arrhythmias caused by such impulse transmissions or generations.

This ablation technique can be and has heretofore been accomplished using an ablation electrode disposed at or near the distal end of an elongated catheter. In use, the catheter containing the ablation electrode is first inserted into, for example, a patient's blood vessel such as the femoral artery or femoral vein. The catheter is manipulated from the insertion site to the heart and then within the heart so as to position the ablation electrode within the heart and into contact with the arrhythmogenic tissue. The approximate location of the ablation electrode is generally monitored noninvasively as, for example, through the use of fluoroscopy or sonography or the like. The precise location of the ablation electrode is determined electrographically by monitoring the electrophysiological signals sensed electronically at the ablation electrode. When the ablation electrode contacts the endocardial tissue through which either an impulse is transmitted at an aberrant time in the heart cycle or at an aberrant location, or at which an ectopic impulse is generated, the electrophysiologist knows the ablation electrode is in contact with the tissue that should be ablated. Once the ablation electrode is properly positioned, energy in the form of either direct current (DC) or radio frequency (RF) current is delivered to the ablation electrode. Such energy is typically delivered to the ablation electrode from an energy source such as a DC defibrillator or an RF unit for generating direct current or radio frequency current, respectively.

In these arrangements, one of the two conductors of the energy source is connected to the ablation electrode and the other conductor is connected to a conductive pad secured to, for example, the parent's back or to at least one return electrode located elsewhere on the catheter. Energy is supplied from the energy source, to the ablation electrode, through the patient, and then returns to the energy source through the conductive pad or the return electrode. Due to the relatively small surface area of the ablation electrode, there is a relatively high current density in the vicinity of the ablation electrode and this high current density causes the region of the body in contact with the ablation electrode to be heated. If the region in contact with the ablation electrode comprises tissue, that tissue is ablated and forms a lesion when the temperature reaches approximately 45° C. to 50° C. Where that contacted tissue is the aberrant pathway or the ectopic focus, as is intended, the pathway is thereby ablated or "open circuited" or the ectopic focus is thereby ablated or disabled. For convenience of description, the region containing the arrhythmogenic tissue to be ablated is referred to hereinafter as the "targeted region". Thus, as used herein, the term "targeted region" is that region, including the endocardium and myocardium, in which ablation of the arrhythmogenic tissue is intended.

As explained hereinbelow, the use of prior art ablation electrodes often results in unintended heating of blood and/or of tissue regions that are not part of the targeted region. If the energized ablation electrode contacts blood and tissue regions and if the temperature of the ablation electrode is permitted to rise above approximately 95° C., the tissue and the blood tend to coagulate and adhere to the ablation electrode. (The adhering tissue plus blood included in the adhering mass is referred to hereinafter as the "coagulum.") The coagulum acts as an insulator which prevents conduction of current from the portion of the electrode to which it adheres. In addition to the detrimental effects on the circulating blood, after a certain amount of coagulum has adhered to the electrode the catheter must be withdrawn from within the patient's body for cleaning of the electrode before proceeding further with the ablation treatment. (These unintended regions of blood and tissue that are often contacted and heated by prior art ablation electrodes are, for convenience, hereinafter collectively referred to as "nontreatment regions". Thus, as used herein the term "nontreatment region" is used to identify a region of blood and/or tissue as to which it is not intended that heat energy be applied by the ablation electrode.) It is known that such nontreatment regions typically have a higher conductance than the targeted region because the nontreatment region provides a broader, and therefore higher conductance, path for current flow than the intended or targeted region.

Heretofore known ablation electrodes have a surface area significantly larger than the endocardial area of the targeted region and not deliberately shaped to match the contours of the endocardial target surfaces of the targeted region. Conventional ablation electrodes have a generally cylindrical contact surface. Referring by way of example to FIGS. 1A and 1B, a presently conventional cylindrically-shaped ablation electrode 4 is shown arranged at the distal end of an electrode catheter 6. The ablation electrode 4 includes an end face or portion 4a having a diameter (D) of, for example, between 2.0 mm and 4.0 mm and an elongated side wall or portion 4b having an elongation or length (L) of, for example, 4.0 mm. Accordingly, the surface area of the end face 4a is in the range of approximately 3 mm$^2$ to 12 mm$^2$ and the surface area of the side wall 4b is in the range of approximately 25 mm$^2$ to 50 mm$^2$. As is therefore readily apparent, the ratio of the surface area of the end face 4a to that of the side wall 4b is in the range of approximately 0.13 to 0.25.

The conventional ablation electrode 4 has several known disadvantages. When such an ablation electrode 4 is placed in contact with the targeted region to perform ablation thereof, a relatively large part of the ablation electrode 4 is in contact with the nontreatment region of blood and tissue surrounding or adjacent to the targeted tissue. By way of example, and as illustrated in FIG. 1A, when the ablation electrode 4 is brought into contact with a targeted region 8, substantially all of the end face 4a may contact the targeted region 8. However, while a relatively minor or insubstantial part of the side wall 4c may also contact the targeted region 8, a substantial or remaining part of the side wall 4b contacts blood 7 and nontreatment region tissue. Prior art ablation procedures are therefore relatively inefficient and typically result in the unintended application of energy to the nontreatment region. Furthermore, the application of energy to the nontreatment region may cause the formation of a larger lesion which could seriously damage the heart. In an attempt to overcome this problem, a greater force is typically applied to the electrode catheter in an effort to place a more substantial part of the side wall 4b in contact with the targeted region 8. However, this technique is difficult to implement and does not effectively overcome the aforementioned problems.

As is known, current flows through all portions of the ablation electrode surface, i.e. both the end face and the side wall, in proportion to the conductance of the targeted and nontreatment regions with which the electrode portions are in contact. As is also known, the nontreatment region has a higher conductance than the targeted region. As explained hereinabove, using the prior art electrode of FIGS. 1A and 1B only the end face 4a of the ablation electrode 4 is in direct contact with the lower conductance targeted region during the ablation procedure whereas the side wall 4b of the ablation electrode 4 is primarily in direct contact with the higher conductance nontreatment region. In other words, there is a tendency for more current to flow from the side wall 4b of the ablation electrode 4 to the nontreatment region than from the end face 4a to the targeted region. Thus, only a relatively small proportion of the current flows into the intended targeted region for therapeutic treatment, while much of the current flows into the unintended nontreatment region. As previously noted, this current flow from the side wall 4a to the nontreatment region causes heating of the blood 7 and tissue which forms coagulum on the ablation electrode 4 and, when enough coagulum has formed on the ablation electrode 4, the electrode catheter must be withdrawn and removed from the patient so that the coagulum may be cleaned from the ablation electrode 4 or the catheter replaced. The (or a new) catheter must then be reinserted and repositioned to the targeted region. However, such removal, reinsertion and repositioning of the catheter can be extremely time consuming and can present further complications for the patient.

As explained above with respect to the prior art electrode of FIGS. 1A and 1B, a significant amount of current flows to the nontreatment region rather than to only the targeted region as intended. As such, the energy source and the electrical conductors (not shown) connecting the electrode to the source must be capable of supplying sufficient energy to both the targeted region for the ablation procedure and to the unintended nontreatment region. As should be apparent, the energy supplied to the nontreatment region does not contribute to the ablation of the arrhythmogenic tissue and, therefore, the energy supply and conductors must be constructed to have a larger capacity than that which is required solely for ablation of the arrhythmogenic tissue.

A further disadvantage of the prior art electrode of FIGS. 1A and 1B is the inability to accurately monitor the temperature at the targeted region. In order to ascertain the effectiveness of the ablation procedure, it is desirable to dynamically monitor the temperature of the ablation electrode using a temperature sensor located at or proximate the targeted region. Generally, such a temperature sensor can be mounted either within the ablation electrode or at the surface of the electrode. In conventional devices, if the temperature sensor is mounted within the electrode, the sensed temperature is generally not that of the targeted region but, rather, a combination of the temperatures of the targeted region and of the nontreatment region. To further complicate matters, the blood generally has a lower temperature due to the cooling effect of constant blood circulation. Alternatively, if the temperature sensor is mounted on the ablation electrode surface, it may be difficult to assure that the sensor is in direct contact with the targeted region. Moreover, the manufacture of such electrodes—i.e. with the sensor on the electrode surface—is difficult and expensive. In either arrangement, the temperature measured is often not an accurate indication of the temperature of the targeted region and is therefore of reduced assistance in sensing or monitoring the temperature of the targeted region.

Another way to assess the effectiveness of the ablation procedure is to monitor the impedance of the ablation electrode circuit. The monitored impedance can provide an indication of when the ablation electrode is in contact with the targeted region since the impedance of cardiac tissue is higher than that of blood. The impedance is monitored by measuring the voltage and current from the energy source and dividing the measured voltage by the measured current; the monitored impedance increases when the ablation electrode is in direct contact with the targeted region. However since, as explained above, the conventional ablation electrode has a relatively large side wall that contacts the nontreatment region, the current flow from the side wall of the ablation electrode is continuously shunted to the low impedance path containing blood so that, even when the ablation electrode moves into contact with the targeted region, there is only a slight increase in the measured circuit impedance which is difficult, at best, to detect. In effect, the low impedance path through the blood-contacting surface of the ablation electrode substantially masks the change in impedance, thereby inhibiting any useful indication that a firm contact between the electrode and the endocardium has been accomplished. More particularly, the circuit impedance that includes the nontreatment region is in the range of 100–150 ohms; and the circuit impedance change for a conventional ablation electrode when a moderate portion contacts endocardial tissue is typically on the order of 10 ohms—i.e., only a 5% to 10% change, which is relatively difficult to measure in the presence of the other causes of impedance fluctuation. Accordingly, impedance monitoring is often ineffective for determining when a conventional ablation electrode is in contact with the targeted region.

As noted above, the prior art electrode catheter comprises a single ablation electrode conductive region that is generally disposed at the very tip of the catheter's distal end. As such, the prior art electrode catheter requires an undue amount of complex manipulation to position the single ablation electrode 4 in contact with the arrhythmogenic tissue. This is particularly significant and becomes more difficult still when there are several targeted regions to be ablated within a patient and each region possesses a different shape and/or curvature or contour.

OBJECTS OF THE INVENTION

The principal object of the present invention is therefore to provide an electrode catheter having an ablation electrode that overcomes the aforementioned disadvantages of the prior art.

It is a particular object of the invention to provide an electrode catheter having an ablation electrode configured to more effectively perform an ablation procedure of the targeted region as rapidly as possible while minimizing damage to the heart.

It is a further object of the present invention to provide an electrode catheter having an ablation electrode with a reduced heating face or surface for avoiding contact with nontreatment regions.

It is an additional object of the present invention to provide an electrode catheter useful for accurately monitoring the temperature of the targeted region.

It is another object of the present invention to provide an electrode catheter having an ablation electrode and a closed loop control system for continuously monitoring the temperature of the targeted region and regulating the current supplied to the ablation electrode in accordance with a desired or "command" temperature.

It is still yet a further object of the invention to provide an electrode catheter in which positioning of the ablation electrode in contact with the targeted region can be accomplished faster and with greater ease than when using prior art electrode catheters.

It is another object of the present invention to provide an electrode catheter useful for accurately identifying contact with the targeted region through impedance measurement.

SUMMARY OF THE INVENTION

According to one aspect of the present invention, an electrode catheter includes an elongated catheter tube having longitudinally spaced apart proximal and distal ends. The catheter carries, preferably although not necessary at or proximate the distal end, an electrically-conductive electrode for ablation of arrhythmogenic tissue in a targeted region of a patient. As used herein, the language "proximate the distal end of the catheter" and the like is intended to denote a location along the catheter closer to its distal end than to its proximal end, and most typically much closer the distal than the proximal end of the catheter. The electrode is, in a first embodiment of the invention, configured in the form of a generally flat disk to substantially conform to the contour of the targeted region so that when the electrode is being operatively positioned in vivo for ablation of the arrhythmogenic tissue, a ratio of the impedance of that portion of the electrode in contact with the targeted region to the impedance of that portion of the electrode in contact with the nontreatment region is greater than approximately 1.5.

A conductive wire is arranged through the elongated catheter tube and is coupled to the electrode. An energy supply source is coupled to the wire at the proximal end of the elongated catheter tube for supplying energy to the electrode for ablation of the arrhythmogenic tissue. The energy supply source supplies either DC energy or radio frequency energy to the electrode. A temperature sensor is located in the electrode for dynamically sensing the temperature of the targeted region, and the energy supply source is made responsive to the temperature sensor by means of a feedback system or arrangement for selectively controlling the amount of energy supplied to the electrode so as to maintain a predetermined or command temperature at the targeted region.

According to another aspect of the present invention, the electrode has a first portion having a first surface area in contact with the targeted region and a second portion having a second surface area in contact with the nontreatment region, the ratio of the first surface area to the second surface area being greater than 1.0.

According to an additional aspect and embodiment(s) of the present invention, an electrode catheter comprises a plurality of ablation electrode conductive regions carried on the catheter. Only the one electrode or conductive region at which the electrogram indicates the passage or generation of an arrhythmogenic signal and which is in contact with the targeted region—i.e. the conductive region whose circuit impedance indicates intimate contact with endocardial tissue—is supplied with energy to ablate the targeted region. This feature may minimize the need to unduly manipulate the catheter so as to place a specific electrode or catheter portion in contact with the targeted region, as is required by prior art electrode catheters which carry only a single conductive region for ablation. Accordingly, the likelihood that one ablation electrode conductive region may be more readily positioned satisfactorily is increased.

According to a still further aspect of the present invention, a method is provided for verifying that the electrode is in contact with the targeted tissue. The method includes the step of providing an electrode catheter having an elongated catheter tube with longitudinally spaced apart proximal and distal ends and an insulated portion on the catheter, preferably at or proximate the distal end thereof. The catheter distal end tip portion comprises a conductive electrode for ablation of targeted tissue in a patient. The conductive electrode has a top, a bottom defining an end face and a side wall therebetween, the insulated portion of the catheter being secured about and in overlapping relation to the upper part of the conductive electrode so that only the end face and a portion of the side wall of the conductive electrode are exposed to tissue and/or blood at the distal end of the electrode catheter. The end face is positioned by moving the catheter so as to displace the conductive electrode from a first position wherein the end face is in contact with a nontreatment region to a second position of contact with the targeted region. The impedance of the electrode circuit is measured in each of the first and second positions. The end face is confirmed to be in contact with the second position, i.e. the targeted tissue, when the measured impedance in the second position is at least about 50% greater than the impedance measured in the first position.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote similar elements throughout the several views:

FIG. 7 is a simplified diagram of a patient undergoing an ablation procedure employing the ablation electrode of the present invention;

FIG. 9 is a simplified diagram of a patient undergoing an ablation procedure employing the ablation electrode of FIG. 8A;

FIG. 11 is a simplified diagram of a patient undergoing an ablation procedure employing the ablation electrode of FIG. 10A.

DETAILED DESCRIPTION OF THE PREFERRED EMBODIMENTS

Figure 1A:
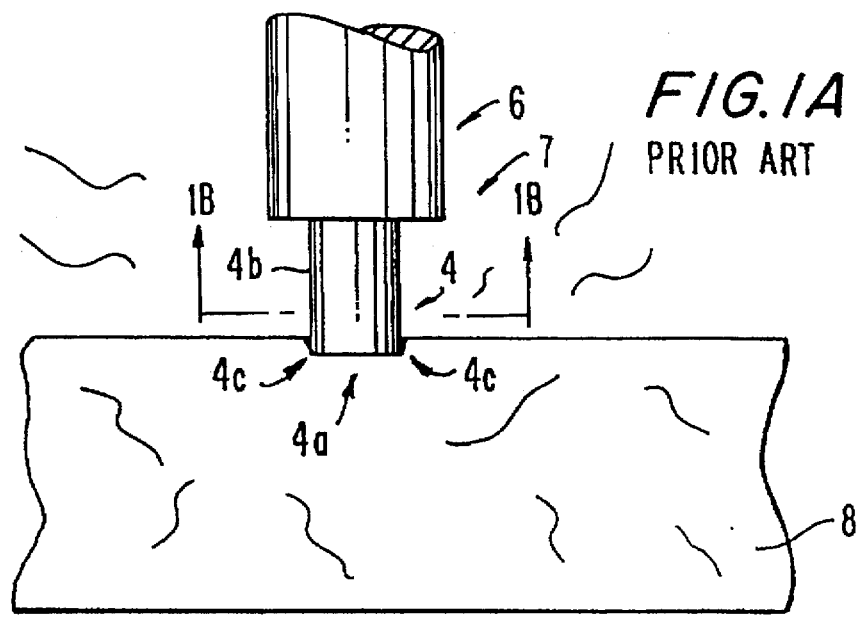
FIGS. 1A and 1B depict a prior art ablation electrode of an electrode catheter.
Figure 1B:
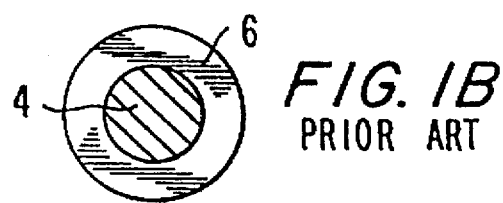
Figure 2:
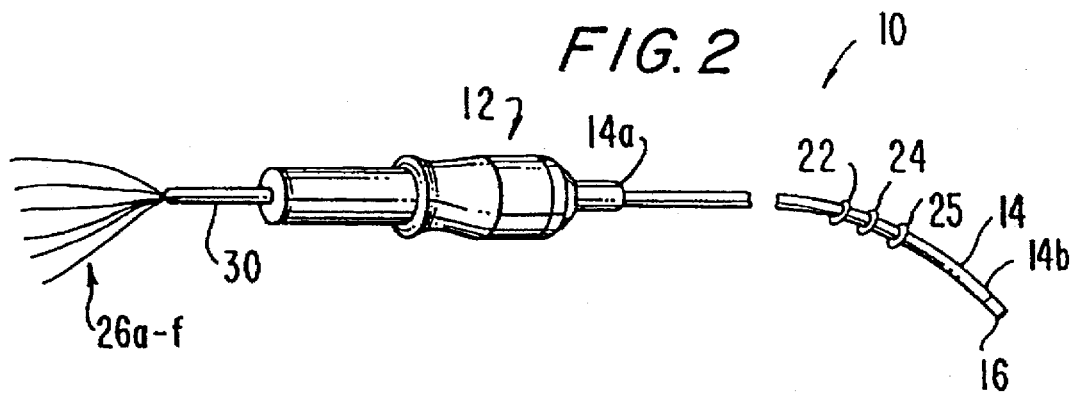
FIG. 2 is a simplified perspective view of an electrode catheter having an ablation electrode constructed in accordance with the present invention.

FIG. 2 depicts a first preferred embodiment of the ablation electrode of the present invention arranged at the end of a generally conventional electrode catheter 10, such as the catheter described in commonly assigned U.S. Pat. No. 5,190,050, the contents of which are incorporated herein by reference. Of course, as will be apparent to those who have read this description, other types of electrode catheters may alternatively be employed.

As shown in FIG. 2, the electrode catheter 10 includes a proximally located handle 12 for remotely manipulating a hollow catheter tube 14 having a proximal end 14a and a distal end 14b. An electrode tip portion 16 is mounted at the distal end 14b, as described in detail hereinbelow. The electrode tip portion 16 is electrically connected to electrical conductor 26f carried through catheter tube 14 for electrical connection to an energy source, as explained hereinbelow. The catheter tube 14 has a length sufficient for insertion through a patient's skin or body orifice and into a blood vessel or other body lumen or cavity or the like so that the electrode tip portion 16 of the catheter tube 14 can be controllably directed into juxtaposition or contact with a particular point or location within the patient's body—as for example arrhythmogenic tissue located within the endocardium or myocardium of the heart. The electrode tip portion 16 may be operatively utilized for ablation of, by way of example, such arrhythmogenic tissue or other malperforming part of the patient's cardiac system.

With continued reference to FIG. 2, electrodes 22, 24 and 25 are integrally carried on the outer surface of catheter tube 14 and are preferably disposed at or proximate the distal end of the tube 14. The electrodes 22, 24 and 25 are preferably fabricated of platinum or stainless steel and may take the form of conductive rings. Insulated electrical wire conductors 26a, 26b, 26c are carried through catheter tube 14 and are electrically connected to the respective electrodes 22, 24 and 25. The other or opposite ends of the conductors 26a, 26b, 26c are connected to suitable heart monitoring instrumentation for detecting and measuring impulses in the heart in a conventional manner. The catheter tube 14 also carries therethrough electrical conductors 26d, 26e which are electrically connected to a temperature sensor 74 (FIG. 3A) as explained in detail hereinbelow.

The electrical conductors 26a–26f may, for example, be implemented as #38 gauge copper conductors having a peripheral coating that electrically insulates the electrical wire conductors one from another and from the catheter tube 14.

FIGS: 3A and 3B illustrate a first and currently most preferred embodiment of the inventive electrode tip portion 16. As seen in these figures, the electrode tip portion 16 comprises an electrode 70. The electrode 70 is formed of a conductive material such as platinum or stainless steel and has somewhat of a funnel-like shape defining a widened tip portion and a relatively narrowed neck portion. An outer shell 20 of the catheter tube 14 is fitted encirclingly about the neck portion of the electrode 70 and is fixedly secured thereto by means of, for example, an adhesive—such as "Output" manufactured by Loctite. The outer shell 20 is fabricated of an electrically insulative material, preferably a nylon coat polymer such as "Pebox" resin manufactured by ATOChem. The outer shell 20 functions as an insulator to at least electrically insulate the neck of the electrode 70 from, by way of example, the nontreatment regions of the patient.

Figure 3A:
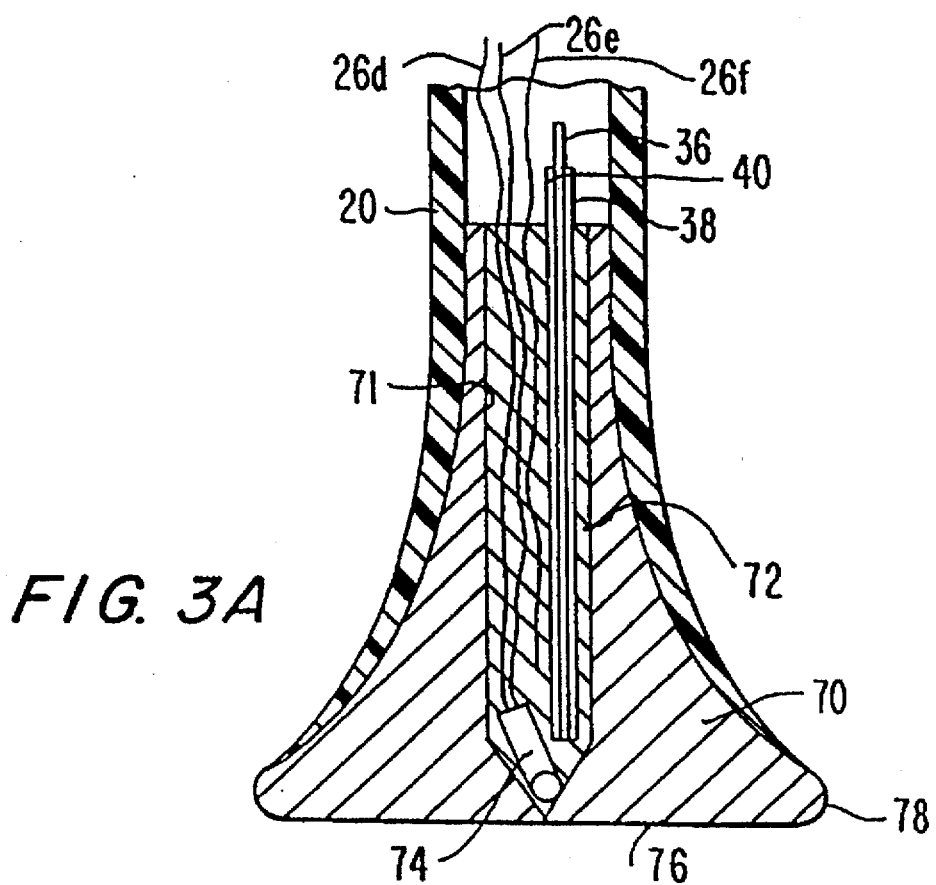
FIG. 3A is a cross-sectional view of a preferred form of the ablation electrode of the present invention.

A bore 71 is defined in and longitudinally along the center of the electrode 70, as for example by drilling. The bore 71 terminates at its distal end—i.e. that closest to the bottom or distal face 76 of the electrode 70—in a generally "V" shaped or conical region. Shims 36, 38 and 40 of the catheter tube 14 are fixedly secured in the bore 71, and electrical conductor 26f is electrically secured in bore 71, as by solder which fills bore 71 and defines a soldered area 72. A hole is then formed in the soldered area 72 to accommodate a temperature sensor 74 which may be implemented using a thermistor, a thermocouple, or an infrared detector or the like. The temperature sensor 74 is located at the distal-most end of the electrode tip portion 16, as shown in FIG. 3A, for accurately measuring the temperature of the targeted region. The temperature sensor 74 is secured in the soldered area 72 by an adhesive and is electrically attached to the electrical conductors 26d, 26e by, for example, soldering.

Figure 3B:
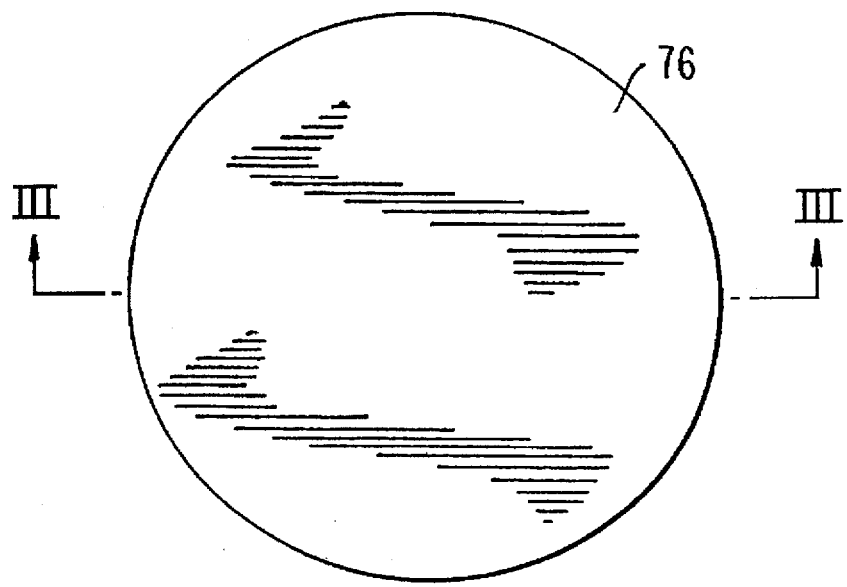
FIG. 3B is a bottom plan view of the ablation electrode of FIG. 3A.
Figure 3C:
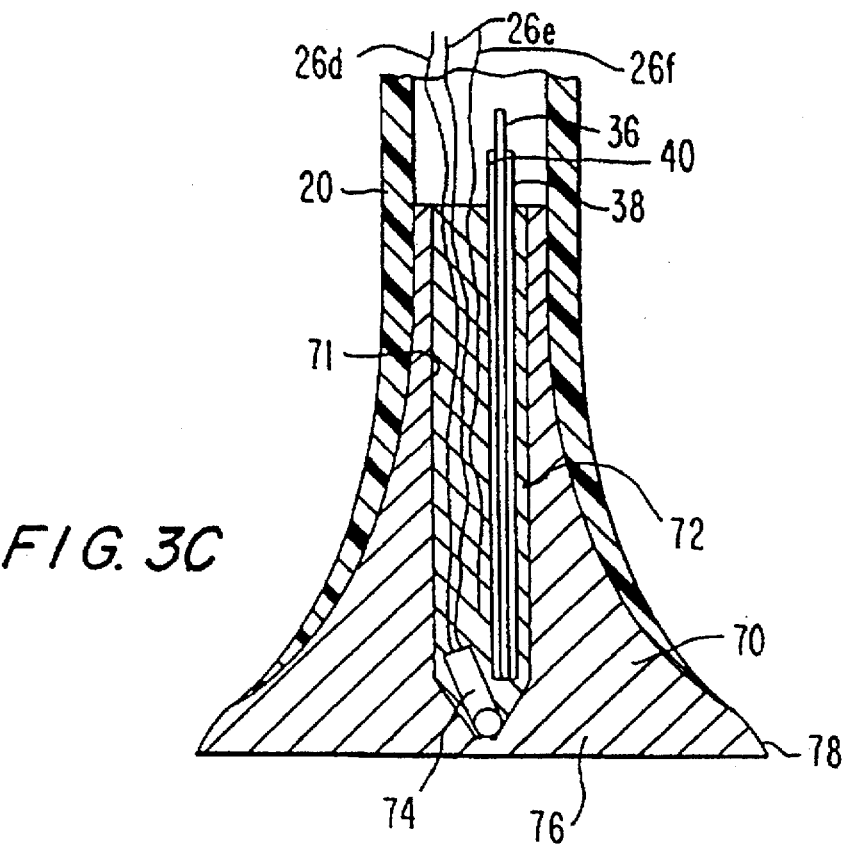
FIG. 3C is a cross-sectional view of the bottom of the ablation electrode taken along the lines III—III of FIG. 3B.
Figure 4:
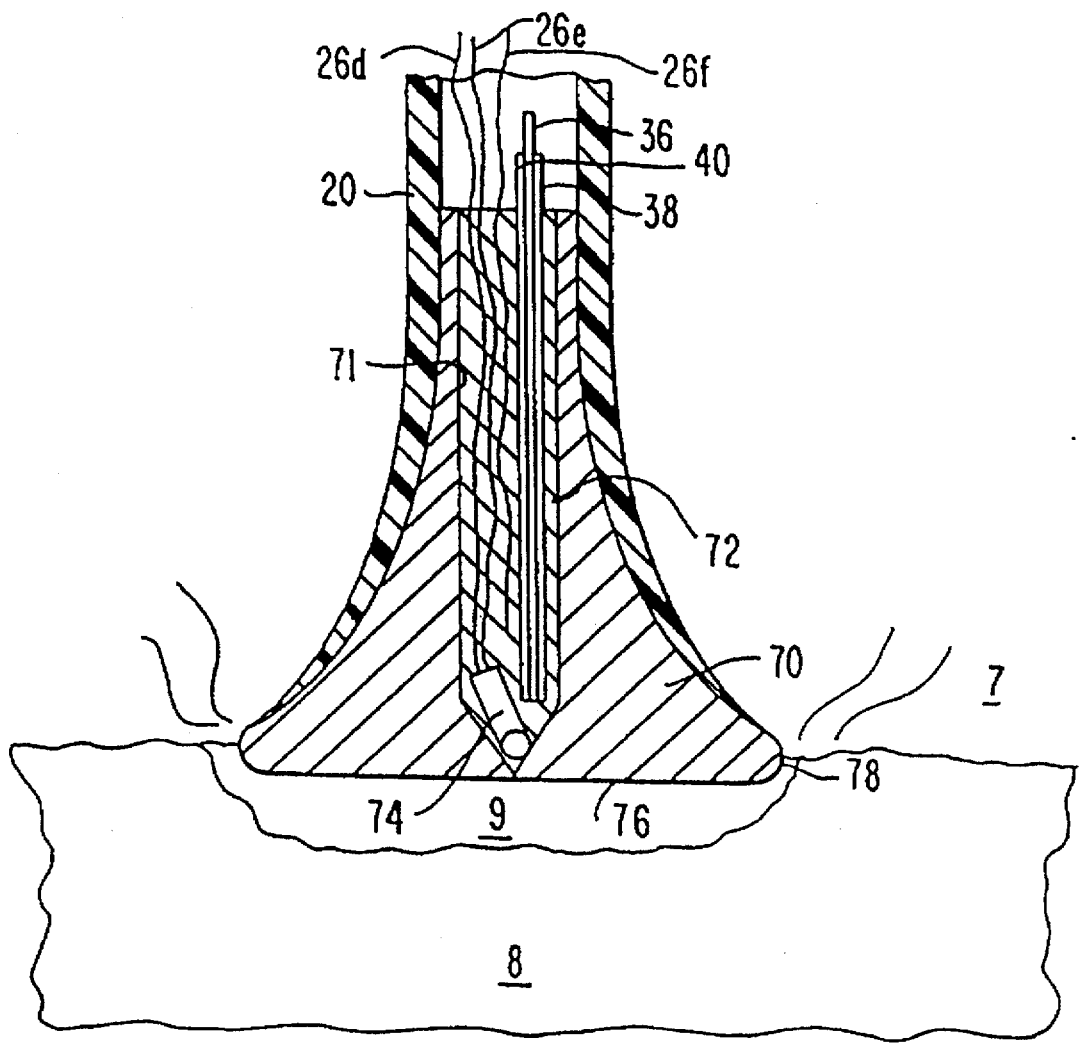
FIG. 4 is a simplified elevational view of the inventive ablation electrode in contact with a targeted region during an ablation procedure.

Referring now to FIGS. 3A-3C, the electrode's distal end face 76 is intended for contact with the targeted region of the patient. Toward that end the end face 76 is advantageously configured to substantially conform to the shape of the targeted region 8 (FIG. 4). With particular reference to FIGS. 3B and 3C, the end face is preferably configured in the shape of a generally flattened disk having a diameter D in the range of approximately 2 to 4 mm, so that the end face 76 defines a first surface area of between approximately 3.14 $mm^2$ to 12.56 $mm^2$. As shown, the electrode 70 also defines a side portion or wall 78 extending from the end face 76 to that point on the electrode 70 at which the distal end of the outer shell 20 is joined to and covers or overlies the electrode 70. The side wall portion preferably has a length L of approximately 0.254 mm that defines a second surface area of between approximately 1.59 $mm^2$ to 3.19 $mm^2$.

Referring now to FIG. 4, during use the electrode 70 is placed in contact with the targeted area 9. As shown in that figure, and owing to the fact that substantially all of the exposed, uninsulated surface areas of the end face 76 and side wall portion 78 are in contact with the targeted region 9, only a de minimis surface area of the side wall portion 78, at most, is in contact with the nontreatment region 7. Moreover, even if a significant part of the exposed surface area of the side wall portion 78 were to be placed in contact with the nontreatment region 7, the effectiveness of the procedure would not be adversely affected because the surface area of the side wall portion 78 is relatively small as compared to the surface area of the end face 76. The ratio of the surface area of the end face 76 to that of the side wall portion 78 is preferably in the range of approximately 1.97 to 3.94, although ratios of at least and preferably greater than 1.0 will achieve notably improved functionability over that of conventional electrode tips which have such ratios in the range of, by way of example, approximately 0.13 to 0.25. In the most preferred embodiment of the invention, the ratio of the surface area of the end face 76 to that of the side wall portion is at least 5 and, optimally, is greater than 10. As will be appreciated by those who have read this disclosure, the larger the surface area of the end face as compared with the surface area of the side wall portion, the better and more controllable the current flow to the targeted region. In other words, when the end face has a larger surface area than the side wall portion, even if no part of the side wall 78 is in contact with the arrhythmogenic tissue most of the current will still flow to the targeted region rather than to the nontreatment region. Thus, in accordance with the preferred embodiment, an ablation procedure of the targeted region can be more effectively performed while minimizing damage to the surrounding or nontreatment region. Moreover, less current is required when using an electrode tip constructed in accordance with the present invention than when using conventional electrode tips.

To further ensure that the surface area of the side wall portion 78 in electrical or electrically-transmissive contact with the nontreatment region 7 is minimized or, ideally, reduced to zero, an electrical insulator such as an epoxy or lacquer is applied or "painted" over the side wall portion 78. In such an arrangement the ratio of the surface area of the end face 76 in contact with the targeted region to the surface area of the side wall portion 78 in contact with the nontreatment region 7 is ideally infinite.

As should now be apparent, by utilizing an electrode having the above-described configuration and construction in accordance with the present invention, substantially all of the current applied to the electrode flows to the targeted region 9 rather than to the adjoining or nontreatment region 7. As a result, damage to the heart is significantly reduced as compared with prior art electrodes. Furthermore, since substantially all of the current flows to the targeted region 9, less current need be supplied to the electrode 70 from the energy supply source 92 through the electrical conductor 26f than with prior art electrodes. Accordingly, the conductor 26f and energy source 92 may be of a smaller capacity, simpler to construct and repair, and less expensive to fabricate and operate than those required for use with prior art electrodes.

As discussed hereinabove, substantially all of the exposed surface areas of the end face 76 and side wall portion 78 of the electrode tip may be placed in contact with the targeted region 9. As a consequence, the temperature sensor 74 can accurately monitor the temperature of the targeted region 9 since there is little or no temperature contribution from the nontreatment region.

Figure 3D:
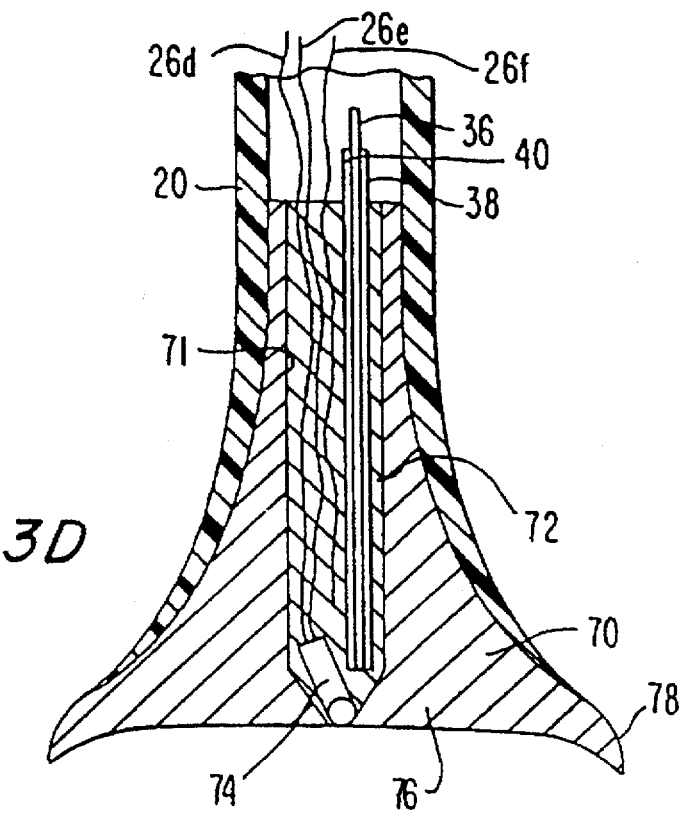
FIGS. 3D and 3E are cross-sectional views similar to FIG. 3C but showing alternate configurations for the bottom face of the ablation electrode.
Figure 3E:
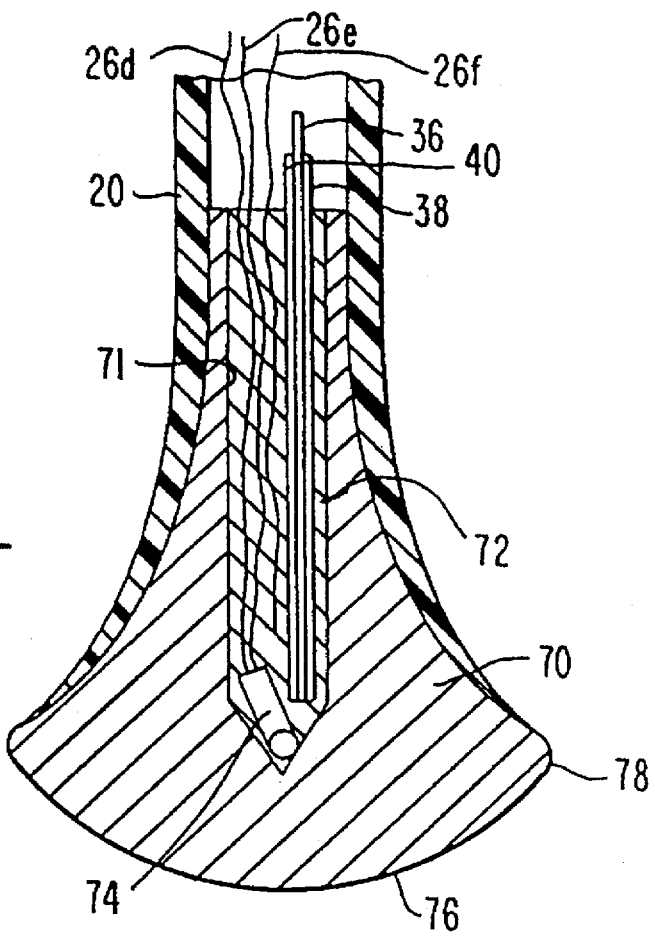
Figure 3F:
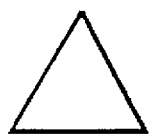
FIGS. 3F–3H are bottom plan views similar to FIG. 3B but showing additional alternate configurations for the ablation electrode of FIG. 3A.
Figure 3G:
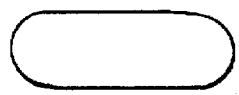
Figure 3H:

Those skilled in the art will now also recognize that the electrode 70—and particularly the end face 76—can take on any appropriate shape so long as the electrode 70 substantially conforms, as is most preferred, to the targeted region such that at least most of the surface area of the electrode tip contacts the targeted region and only a de minimis surface area, at most, contacts the nontreatment region. In other words, the electrode 70 is preferably fabricated to assume, at least at its intended contact portion, the size and shape and contour of the targeted region. In the currently most preferred embodiment, and as explained above, the distal end of the electrode 70 has a circular disk shape to conform to a targeted area having substantially the same general shape. In an alternate form shown in FIG. 3D, the end face 76 may have a generally concave contour to substantially conform to the contour of the targeted region, such as a targeted surface in the vicinity of a heart valve. FIG. 3D illustrates still another embodiment in which the electrode 70 has a substantially convex contour shape. Of course, whatever the flatness or concavity or other contour of the end face 76 of the electrode 70, the electrode need not have a circular peripheral shape unless such circularity is appropriate to the shape of the targeted region to be ablated. Thus, it is contemplated that the electrode 70 may, by way of example and not limitation, alternatively be triangular (FIG. 3F), or elliptical (FIG. 3G), or rectangular (FIG. 3H) in shape. Moreover, since only the end face 76 should contact the targeted region to effectuate the ablation thereof, less force is required to maintain the electrode 70 in the intended direct contact than is required by or necessary for effective use of prior art devices.

Figure 5A:
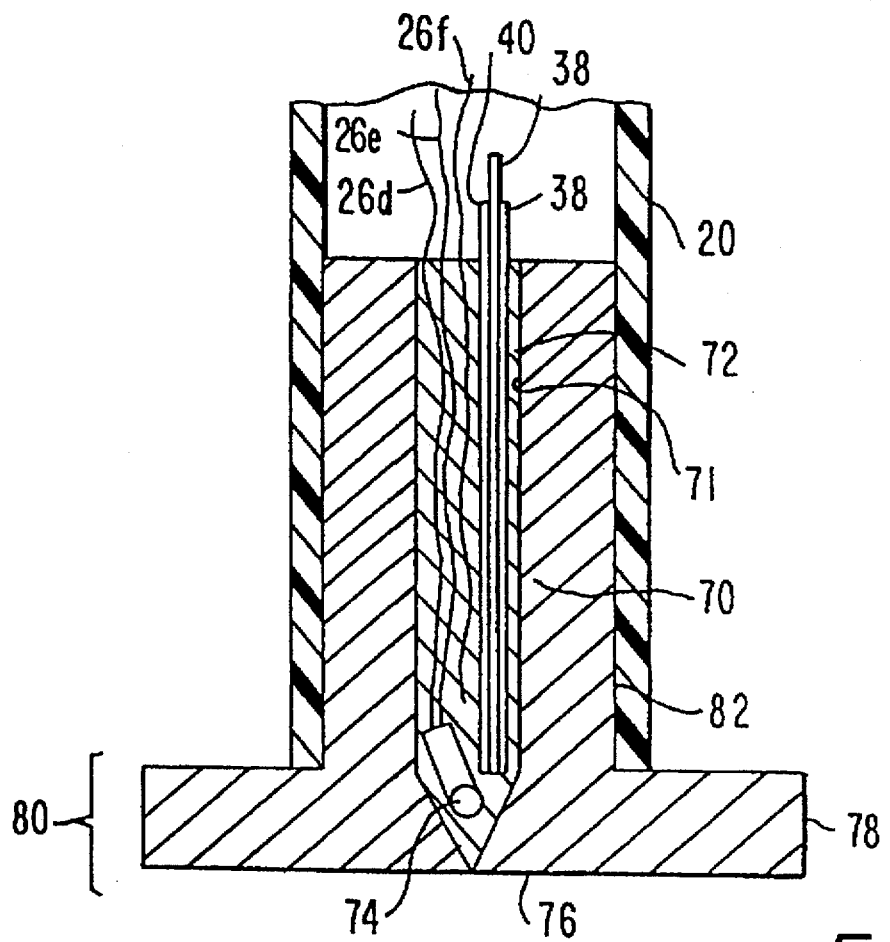
FIG. 5A is a cross-sectional view of an ablation electrode constructed in accordance with a second embodiment of the invention.
Figure 5B:
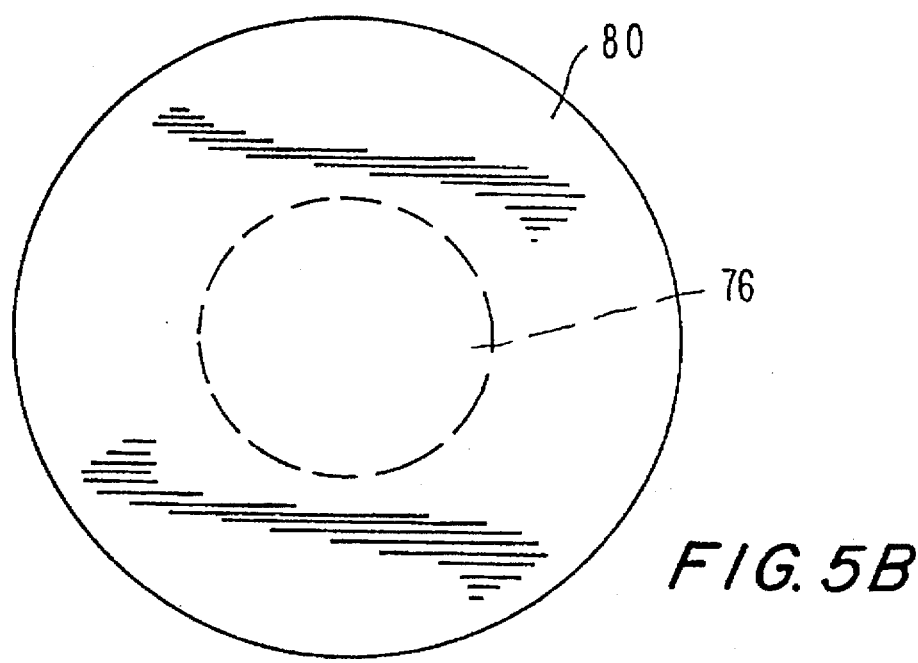
FIG. 5B is a bottom plan view of the ablation electrode of FIG. 5A.

FIGS. 5A and 5B illustrate an alternate embodiment of an electrode tip constructed in accordance with the teachings of the present invention. As shown in these figures, the electrode 70 is shaped as an inverted T-shaped "nail" and comprises a head portion 80 and a neck portion 82, the head portion being configured to generally conform in shape and, preferably, contour to the targeted region. The outer shell 20 of the catheter 12 is disposed in covering or overlying relation with substantially the entire neck portion 82 and is secured thereto as by an adhesive. Like the first embodiment of FIG. 3 described hereinabove, the shims 36, 38, 40 and the electrical conductor 26f are attached to the electrode 70 by soldering or the like, and the temperature sensor 74 is disposed in a bore defined in the soldered area and is adhesively or otherwise attached thereto. In this alternate embodiment, the thickness of the head is approximately 0.254 mm and the head diameter is between approximately 2 and 4 mm. It will be appreciated, therefore, that as in the embodiment of FIG. 3, the surface area of the end face 76 of the electrode tip is larger than the surface area of the side wall portion 78. Thus, most—or virtually all—of the electrical current or energy will flow from the electrode 70 to the targeted region rather than to the nontreatment region, resulting in a notably more efficient and less harmful ablation procedure than has conventionally been heretofore possible.

Figure 6A:
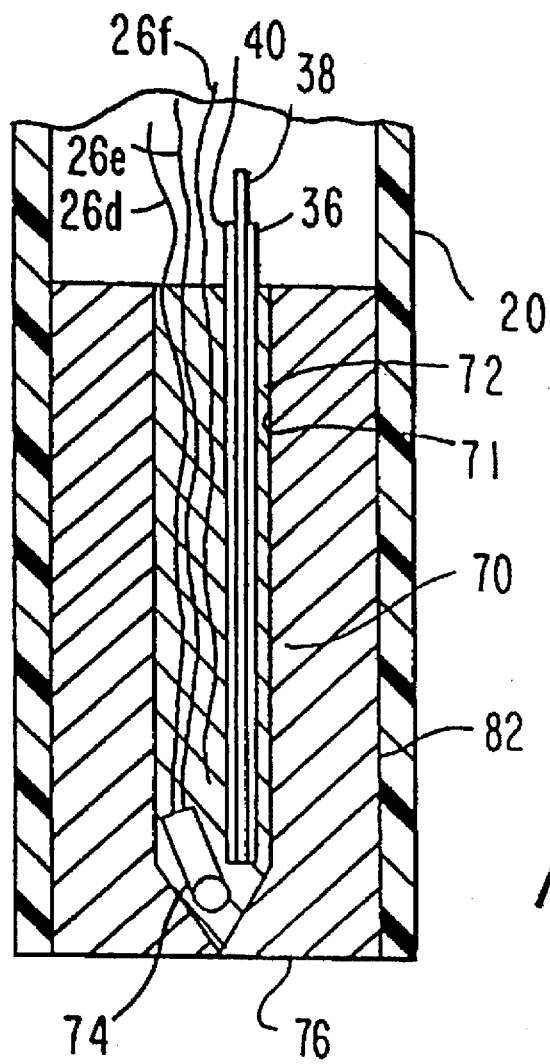
FIG. 6A is a cross-sectional view of an ablation electrode constructed in accordance with a third embodiment of the present invention.
Figure 6B:
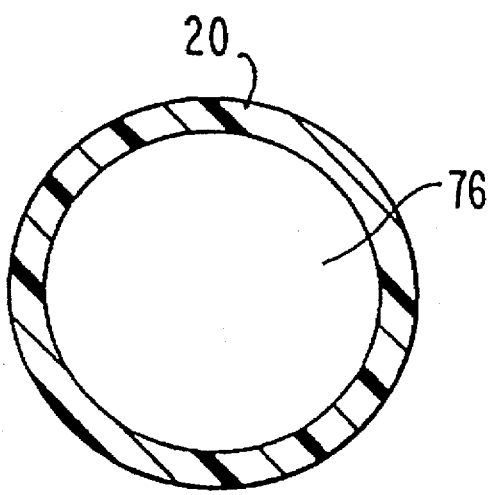
FIG. 6B is a bottom plan view of the ablation electrode of FIG. 6A.

FIGS. 6A and 6B illustrate yet another embodiment of an electrical ablation tip constructed in accordance with the present invention. As seen in FIG. 6A, the electrode 70 is in the general form of a cylinder. The outer shell 20 of the catheter 12 is fitted about the neck portion 82 of the electrode 70 such that only the end face 76 is exposed, substantially the entire neck portion 82 being electrically insulated from the nontreatment and targeted regions by the outer shell 20 of the catheter tube 14. In this third major embodiment the ratio of the area of the end face 76 to that of the exposed or uninsulated (and therefore conductive) neck portion 82 ideally approaches infinity.

In FIG. 7, an electrical energy source 92 is shown connected to the proximal end of the electrical conductor 26f for supplying energy to the inventive electrode 70. The energy thus supplied may be either DC shocks or RF pulses and the energy source 92 may, by way of example, be a radio frequency generator Model RFG-3C manufactured by Radionics. The electrical energy source 92 is also connected to the proximal end of the electrical conductors 26d, 26e, the distal or opposite ends of which are connected to the temperature sensor 74 for monitoring the temperature at the electrode 70. The electrical energy source 92 is additionally connected to a conductive pad 94, via an electrical conductor 90, secured to the back of the patient in a known manner, as by an adhesive (not shown).

The electrical energy source 92 includes an output device or indicator assembly for displaying or outputting, among other parameters, the current supplied to the electrode, the output voltage, the output power, the calculated impedance and the temperature at the electrode 70. The display may, for example, take the form of liquid crystal displays, light emitting diode displays, analog meters, or a CRT or the like. The electrical energy source 92 will typically also include an input for setting, among other parameters, a temperature set point, a treatment duration, a current set point and a voltage set point.

In operation, the electrode tip portion 16 of the catheter tube 14 is typically first inserted into a patient lumen such as a blood vessel or the urethra. The location of the tip portion 16 within the patient is typically monitored noninvasively such, for example, as through the use of X-rays or sonography or the like. The tip portion 16 of catheter tube 14 is precisely positioned or directed to the targeted region (herein assumed, for ease of description, to be within the heart) in a known manner. As the electrode 70 is being positioned in the heart, the heart's impulses are detected by the electrodes 22, 24, 25 which are connected to a suitable heart monitoring instrument 96. The arrhythmogenic tissue is located and identified upon the detection of abnormal impulses by the heart monitoring instrument 96.

When the electrode 70 is precisely positioned at and with the end face 76 in contact with the targeted region, electrical energy is supplied by the electrical energy source 92 to the electrode 70. This is accomplished by inputting either the voltage and current set points or the desired temperature for a specified duration. Since the temperature sensor 74 provides an accurate indication of the temperature of the targeted region, the temperature can be dynamically monitored to manually control the treatment voltage, current and duration. Alternatively, a temperature set point may be inputted. In this latter mode, the electrical energy source determines the voltage and current required to produce the desired temperature and periodically adjusts the voltage and/or the current to maintain the desired temperature based on the actual temperature sensed by the temperature sensor 74. As the current flows from the electrode 70 to the targeted region, the arrhythmogenic tissue is heated and, when heated to approximately 45° C. to 50° C., it is destroyed. However, because blood tends to coagulate at about 95° C., the maximum temperature set point is preset to between 75° C. to 85° C. so as to avoid excessive heating and to ensure ablation of the arrhythmogenic tissue without forming coagulum on the ablation electrode.

As previously noted, the circuit impedance when the electrode 70 is in contact with the nontreatment region is different from the circuit impedance when the electrode 70 is in contact with the targeted region, thereby providing a mechanism for verifying proper positioning of the electrode. It will be recalled that the impedance of the nontreatment region is about 100 to 150 ohms, whereas the impedance of the arrhythmogenic tissue is at least about 50% greater. In the preferred embodiments of the invention the impedance is displayed on the energy supply source 92. Since the end face 76 of the inventive electrode 70 substantially conforms to the shape of the targeted region, when the electrode 70 is moved into direct contact with the targeted region there will be an increase of about 50–225 ohms or 50% to 150% in the sensed impedance. In other words, the ratio of the impedance at the targeted region to that at the nontreatment region is typically between approximately 1.5 to 2.5. Based on this impedance change it is possible to readily determine, with a reasonable degree of certainty, when the end face 76 of the electrode 70 of the invention is in contact with the targeted region; this ability is in stark contrast to the sensed impedance change using prior art electrodes with which, as previously noted, one obtains an increased impedance of only between about 5% and 10%.

Figure 8A:
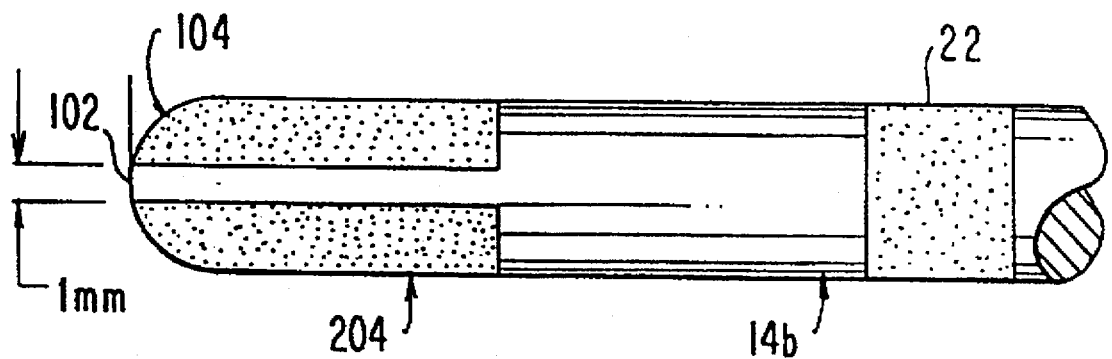
FIG. 8A is a side view of the distal end of an electrode catheter carrying a plurality of ablation electrode conductive regions in accordance with a third embodiment of the invention.
Figure 8B:
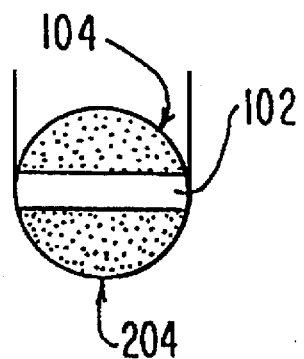
FIG. 8B is a bottom plan view of the electrode catheter distal end of FIG. 8A.

FIGS. 8A and 8B illustrate a third embodiment of an electrode catheter tip or distal end constructed in accordance with the teachings of the present invention. As shown in these figures, the electrode catheter carries two ablation electrodes or conductive regions 104 and 204 in the form of two substantially semi-circular cylindrical sections arranged at or proximate the distal end 14b of the catheter tube 14. Similar to the preferred embodiment shown in FIG. 2, a sensing electrode 22 is integrally carried on the outer surface of catheter tube 14 and is preferably disposed at or proximate the distal end of the tube 14. As best seen in FIG. 9, one end of the electrical wire 26a is carried through catheter tube 14 and is electrically connected to the electrode 22 and the other or opposite end of the conductor 26a is connected to a suitable heart monitoring instrument 96 for detecting and measuring impulses in the heart in a conventional manner. The ablation electrodes 104, 204 are electrically and thermally insulated from each other by an insulating portion 102 arranged on the electrode catheter tube 14. The ablation electrodes 104, 204 each include a respective temperature sensor (not shown) for monitoring the temperature of the corresponding ablation electrode. Referring again to FIG. 9, the ablation electrodes 104, 204 are electrically connected to selection and energy source 92' by electrical conductors 26f and 26f', respectively, and the temperature sensors are connected thereto by electrical conductors 26d, 26e and 26d', 26e', respectively. The selection and energy source 92' is constructed and operates in a manner similar to the electrical energy source 92 depicted in FIG. 7 and described above. Additionally, the selection and energy source 92' includes a selection circuit for selecting an appropriate one of the ablation electrodes 104, 204, along with its corresponding temperature sensor. In use, the impedance of each electrode 104, 204 is monitored as the ablation electrode is manipulated within the heart, as noted above. The electrode is selected when its corresponding change of impedance indicates that it is in contact with the targeted region. Energy is then supplied to the selected electrode to ablate the targeted region. By virtue of this arrangement, the ablation electrode may be more easily and rapidly positioned than is conventionally possible.

Figure 10A:
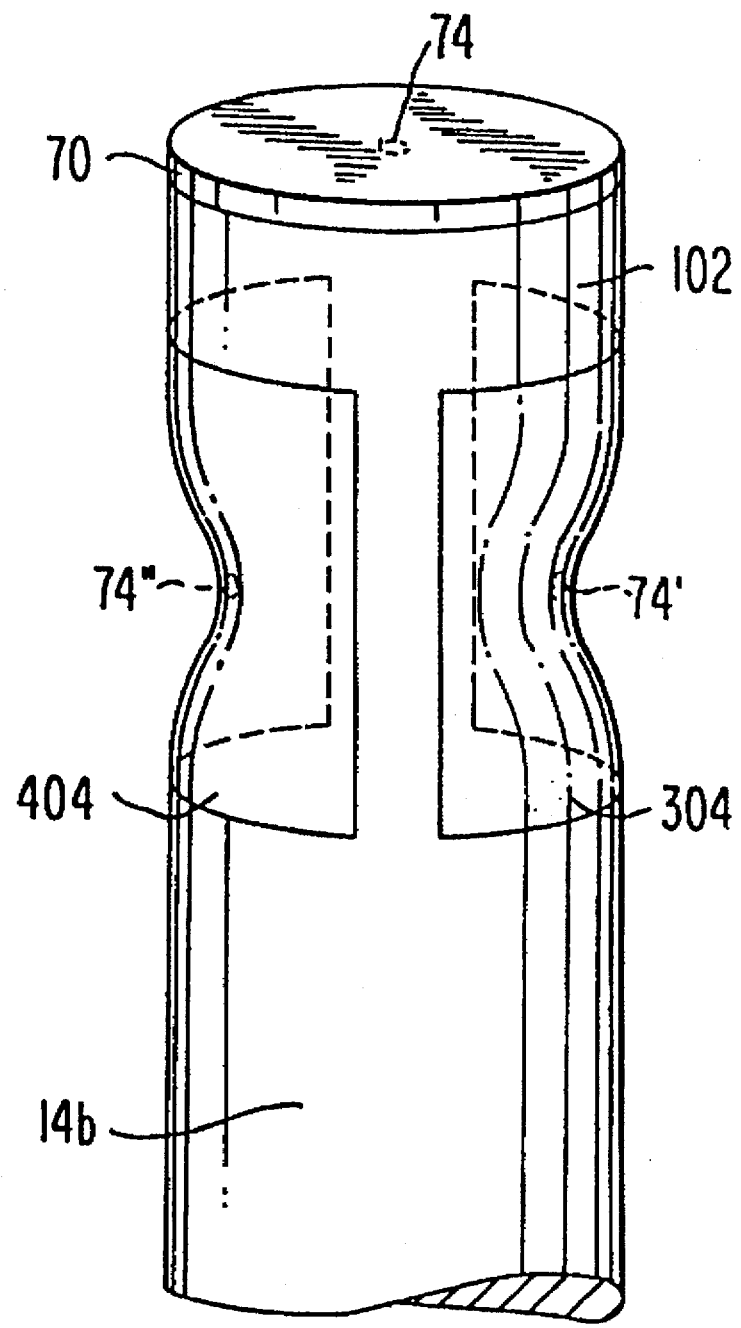
FIG. 10A is a perspective view of the distal end an electrode catheter carrying a plurality of ablation electrode conductive regions in accordance with a fourth embodiment of the invention.
Figure 10B:
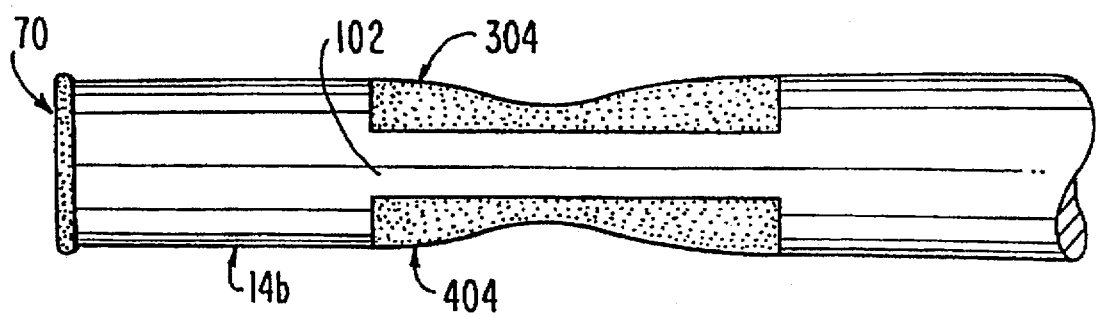
FIG. 10B is a side view of the electrode catheter distal end of FIG. 10A.
Figure 10C:
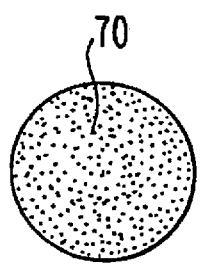
FIG. 10C is a bottom plan view of the electrode catheter distal end of FIG. 10A.

FIGS. 10A, 10B and 10C illustrate a fourth embodiment of an electrode catheter tip or distal end or portion proximate the catheter distal end constructed in accordance with the teachings of the present invention. As shown in these figures, the electrode catheter carries an end-located ablation electrode 70 similar to that depicted in FIGS. 5A and 5B and described hereinabove. In addition, the electrode catheter is provided with two further ablation electrodes 304, 404 carried on a peripheral wall at the distal end 14b of the catheter tube 14 and extending circumferentially about a fractional portion of the catheter periphery. It should be pointed out that the electrodes 304, 404 may also and/or alternatively be positioned along the catheter at locations substantially remote from the catheter distal end, although it is contemplated and generally intended that the ablation electrodes be disposed closer to the distal end than to the proximal end of the electrode catheter. As shown in FIGS. 10B and 10C, the ablation electrodes 304, 404 each have a somewhat concave contour to substantially conform to the generally convex contour of a targeted region. Of course, as previously explained, the ablation electrodes or conductive portions may be of any suitable shape which conforms to the shape and/or contour of the targeted region. The ablation electrodes 304, 404 are electrically and thermally insulated from each other by an insulating portion 102 arranged on or otherwise forming a part of the electrode catheter tube 14. The ablation electrodes 70, 304 and 404 each include temperature sensors 74, 74' and 74", respectively, for monitoring the temperature of the corresponding ablation electrode. As best seen in FIG. 11, the ablation electrodes 70, 304 and 404 are individually electrically connected to selection and energy source 92' by electrical conductors 6f, 26f' and 26f", respectively, and the temperature sensors are individually connected to the source 92' by electrical conductors 26d, 26e, 26d' 26e' and 26d", 26e", respectively. The selection and energy source 92' is constructed and operates similarly to that depicted in FIG. 9 and described hereinabove. As will now be apparent to those who have read this description, the electrode catheter according to the present invention may carry any suitable number of ablation electrodes or conductive regions individually selectable by the user for selectively ablating targeted regions, and the depiction of three ablation electrodes in the embodiment illustrated in FIGS. 10A, 10B and 10C is for illustrative purposes only. In addition, the ablation electrode(s)—of whatever size(s), shape(s), contour(s) and/or quantity—may be carried at any suitable location(s) along the catheter although, as previously pointed out, it is generally contemplated and anticipated that the ablation electrodes will be disposed at or proximate, as herein defined, the distal end of the catheter.

Thus, while there have been shown and described and pointed out fundamental novel features of the invention as applied to various preferred embodiments thereof, it will be understood that various omissions and substitutions and changes in the form and details of the disclosed apparatus and methods may be made by those skilled in the art without departing from the spirit of the invention. It is the intention, therefore, to be limited only as indicated by the scope of the claims appended hereto.

What is claimed is:

1. An electrode catheter, comprising:
   an elongated catheter tube having proximal and distal ends and an insulated portion at the distal end thereof; and
   a catheter tip portion comprising conductive electrode means carried at the distal end of the tube for ablation of targeted tissue in a patient, said conductive electrode means comprising a bottom face and a sidewall extending proximally from the bottom face, said insulated portion of said catheter tube being secured about a first portion of the sidewall such that said bottom face and a second portion of said sidewall of said electrode means are exposed at the distal end of said elongated catheter tube, said bottom face defining an end face having a first surface area intended for contact with the targeted tissue and said second portion of said sidewall defining a second surface area, the ratio of the first surface area to the second surface area being greater than 1;
   wherein a ratio of a first impedance of a circuit comprising said conductive electrode means when said end face is in contact with the targeted tissue to a second impedance of said circuit when said end face is in contact with a nontreatment region is greater than approximately 1.5.

2. A catheter according to claim 1, wherein said end face is configured in a shape selected from the group consisting of a disk, an ellipse and a polygon.

3. A catheter according to claim 2, wherein said end face has a substantially concave contour.

4. A catheter according to claim 2, wherein said end face has a substantially convex contour.

5. A catheter according to claim 1, further comprising energy supply means coupled to said electrode means at the proximal end of said catheter tube for supplying energy to said conductive electrode means for ablation of the targeted tissue.

6. A catheter according to claim 5, further comprising wiring means extending through said elongated catheter tube for conductively coupling said conductive electrode means to said energy supply means.

7. A catheter according to claim 6, further comprising a temperature sensing means disposed in the bottom of said conductive electrode means for sensing a temperature of the targeted tissue.

8. A catheter according to claim 7, wherein said energy supply means is operatively responsive to said temperature sensing means for maintaining a predetermined temperature of the targeted tissue.

9. A catheter according to claim 5, wherein said energy supply means supplies one of DC energy and radio frequency energy to said conductive electrode means.

10. A catheter according to claim 1, wherein said ratio of the first surface area to the second surface area is greater than 5.

11. A catheter according to claim 1, wherein said ratio of the first surface area to the second surface area is greater than 10.

12. A catheter tip portion for dependency from a distal end of an electrode catheter, comprising:

conductive electrode means for ablation of targeted tissue in a patient, said conductive electrode means comprising a bottom face and a sidewall extending proximally from the bottom face, said bottom face defining an end face having a first surface area intended for contact with the targeted tissue and said sidewall defining a second surface area, the ratio of the first surface area to the second surface area being greater than 1;

wherein a ratio of a first impedance of a circuit comprising said conductive electrode means when said end face is in contact with the targeted tissue to a second impedance of said circuit when said end face is in contact with a nontreatment region is greater than 1.5.

13. A catheter tip portion according to claim 12, wherein said end face is configured in a shape selected from the group consisting of a disk, an ellipse and a polygon.

14. A catheter tip portion according to claim 13, wherein said end face has a substantially concave contour.

15. A catheter tip portion according to claim 12, further comprising energy supply means coupled to said electrode means for supplying energy to said conductive electrode means for ablation of the targeted tissue.

16. A catheter tip portion according to claim 12, wherein said ratio of the first surface area to the second surface area is greater than 5.

17. A catheter tip portion according to claim 12, wherein said ratio of the first surface area to the second surface area is greater than 10.

18. In a method for ablating targeted tissue in a patient, a method of confirming that an end face of a catheter is in contact with the targeted tissue, comprising the steps of:

providing an electrode catheter comprising:

an elongated catheter tube having proximal and distal ends and an insulated portion at the distal end thereof, and a catheter tip portion comprising conductive electrode means carried at the distal end of the tube for ablation of targeted tissue in a patient, the conductive electrode means comprising a bottom face and a sidewall extending proximally from the bottom face, the insulated portion of the catheter tube being secured about a first portion of the sidewall such that the bottom face and a second portion of the sidewall of the conductive electrode means are exposed at the distal end of the elongated catheter tube, the bottom face defining an end face for contact with the targeted tissue, and such that a ratio of a first impedance of a circuit comprising said conductive electrode means when the end face is in contact with the targeted tissue to a second impedance of said circuit when the end face is in contact with a nontreatment region is greater than 1.5;

positioning the end face by moving the conductive electrode means from a first position wherein the end face is in contact with a nontreatment region to a second position;

measuring the impedance of a circuit comprising the conductive electrode means at the first and second positions; and confirming that the end face is in contact with the targeted tissue in the second position when the impedance measured in said measuring step in the second position is at least approximately 50% greater than the impedance measured in the first position.

19. In a method according to claim 18, further comprising the step of supplying energy to the conductive electrode means for ablation of the targeted tissue.

20. In a method according to claim 19, further comprising the step of sensing the temperature of the targeted tissue.

21. A method according to claim 20, further comprising the step of controlling the supply of energy in said supplying step to the conductive electrode means in accordance with the temperature sensed in said sensing step to maintain a predetermined temperature at the targeted tissue.

22. A method for ablating targeted tissue of initially unknown size and shape within a patient's body, comprising the steps of:

(a) determining the shape of the targeted tissue;

(b) selecting a conductive electrode to conform to said shape of the targeted tissue determined in said step (a), said conductive electrode being of fixed size and shape and carried on an elongated catheter tube;

(c) positioning said elongated catheter tube so that said conductive electrode selected in said step (b) is positioned within the patient's body in complementary contact with the targeted tissue; and (d) supplying energy to said selected conductive electrode to ablate the targeted tissue.

23. An electrode catheter for ablating targeted tissue within a patient's body, the targeted tissue having a predetermined shape, said electrode catheter comprising:

an elongated catheter tube having proximal and distal ends and an insulated portion arranged proximate said distal end of the catheter tube;

a plurality of electrically-conductive ablation electrodes arranged proximate said distal end of said elongated catheter tube for placement against target tissue to be ablated and variously shaped to conform to anticipated shapes of target tissue to be ablated through contact with the target tissue, said plurality of ablation electrodes being electrically and thermally insulated from one another by said insulated portion; and means for selecting one of said plurality of ablation electrodes that most closely conforms to the predetermined shape of the targeted tissue and for supplying energy to said selected one of said ablation electrodes for ablating the targeted tissue.

24. An electrode catheter according to claim 23, wherein at least one of said plurality of electrically-conductive ablation electrodes is carried at said distal end of said elongated catheter tube.

25. An electrode catheter according to claim 23, wherein said plurality of electrically-conductive ablation electrodes comprise first and second electrodes carried at said distal end of said elongated catheter, wherein said first and second electrodes are electrically and thermally insulated from each other by said insulated portion.

26. An electrode catheter according to claim 23, wherein said elongated catheter tube has a distal region proximate said distal end, and wherein said plurality of electrically-conductive ablation electrodes comprise a peripheral electrode carried on a peripheral wall at said distal region and extending about a fractional portion of a periphery of said elongated catheter tube, said electrically-conductive ablation electrode having a shape substantially conforming to the predetermined shape of the targeted tissue.

27. An electrode catheter according to claim 23, wherein at least one of said plurality of electrically-conductive ablation electrodes is configured in a shape selected from the group consisting of a disk, an ellipse, a semi-circle and a polygon.

28. An electrode catheter according to claim 23, wherein at least one of said plurality of electrically-conductive ablation electrodes has a contour selected from a substantially concave contour and a substantially convex contour.

29. An electrode catheter according to claim 23, wherein each of said plurality of electrically-conductive ablation electrodes comprises a respective temperature sensor for monitoring the temperature of each ablation electrode, and wherein said means for supplying energy is operatively responsive to said temperature means of the selected ablation electrode for maintaining a predetermined temperature of the targeted tissue.

30. An electrode catheter for ablating targeted tissue within a patient's body, said targeted tissue having a predetermined shape and size, said electrode catheter comprising:

an elongated catheter tube comprising an insulated portion and having proximal and distal ends and a distal region proximate said distal end;

a first electrically-conductive ablation electrode carried on a peripheral wall at said distal region and extending about a fractional portion of a periphery of said elongated catheter tube, said first electrically-conductive ablation electrode being configured so as to have a shape substantially conforming to the predetermined shape of the targeted tissue:

an electrically-conductive ablation tip electrode carried at the distal end of said elongated catheter tube, wherein said ablation tip electrode is electrically and thermally insulated from said first ablation electrode by said insulated portion; and means for selecting the one of said first ablation electrode and said ablation tip electrode that most closely conforms to at least one of the predetermined shape and size of the targeted tissue and for supplying energy to said selected electrode for ablating the targeted tissue.

31. An electrode catheter according to claim 30, wherein said electrode catheter further comprises:

a second electrically-conductive ablation electrode carried on a peripheral wall of the catheter tube at said distal region and extending about a fractional portion of a periphery of said elongated catheter tube, said second ablation electrode being electrically and thermally insulated and separated from said first ablation electrode by said insulated portion; and wherein said means for selecting further comprises means for selecting the one of said first and second ablation electrodes and said ablation tip electrode that most closely conforms to at least one of the predetermined shape and size of the targeted tissue and for supplying energy to said selected one electrode for ablating the targeted tissue.

32. An electrode catheter according to claim 31, wherein at least one of said first electrically-conductive ablation electrode, said second electrically-conductive ablation electrode, and said electrically-conductive ablation tip electrode has a contour selected from a substantially concave contour and a substantially convex contour.

* * * * *